(12) United States Patent
Gavard Molliard

(10) Patent No.: US 8,574,629 B2
(45) Date of Patent: Nov. 5, 2013

(54) INJECTABLE HYDROGEL WITH AN ENHANCED REMANENCE AND WITH AN ENHANCED ABILITY TO CREATE VOLUME

(75) Inventor: Samuel Gavard Molliard, Bogeve (FR)

(73) Assignee: Anteis S.A., Plan-les-Ouates, Geneva (CH)

( * ) Notice: Subject to any disclaimer, the term of this patent is extended or adjusted under 35 U.S.C. 154(b) by 422 days.

(21) Appl. No.: 12/512,581

(22) Filed: Jul. 30, 2009

(65) Prior Publication Data

US 2010/0028435 A1    Feb. 4, 2010

(30) Foreign Application Priority Data

Aug. 1, 2008 (FR) ...................... 08 04416

(51) Int. Cl.
- A61K 8/64 (2006.01)
- A61L 9/14 (2006.01)
- A61K 8/73 (2006.01)

(52) U.S. Cl.
USPC ........................... 424/486; 424/499; 424/501

(58) Field of Classification Search
None
See application file for complete search history.

(56) References Cited

U.S. PATENT DOCUMENTS

| | | | |
|---|---|---|---|
| 5,399,351 A * | 3/1995 | Leshchiner et al. | 424/422 |
| 5,800,541 A | 9/1998 | Rhee et al. | |
| 6,685,963 B1 * | 2/2004 | Taupin et al. | 424/486 |
| 2004/0127698 A1 | 7/2004 | Tsai et al. | |
| 2005/0069572 A1 | 3/2005 | Williams et al. | |
| 2005/0136122 A1 | 6/2005 | Sadozai et al. | |
| 2006/0194758 A1 * | 8/2006 | Lebreton | 514/54 |
| 2006/0246137 A1 | 11/2006 | Hermitte et al. | |
| 2007/0196426 A1 | 8/2007 | Hermitte et al. | |

FOREIGN PATENT DOCUMENTS

| | | |
|---|---|---|
| EP | 2 011 816 | 1/2009 |
| EP | 2011816 A1 * | 1/2009 |
| FR | 2 733 426 | 10/1996 |
| WO | 00/01428 | 1/2000 |
| WO | 2004/092222 | 10/2004 |
| WO | WO 2005020849 A2 * | 3/2005 |
| WO | 2005/085329 | 9/2005 |
| WO | 2005/012364 | 2/2008 |

OTHER PUBLICATIONS

O'Donnell, Polyols as formulation problem solvers, Feb. 1996.*
EP 2011816 published on Jan. 7, 2009; abstract & machine translation.*
French Search Report date May 28, 2009, from corresponding French application.

* cited by examiner

Primary Examiner — Robert A Wax
Assistant Examiner — H. Sarah Park
(74) Attorney, Agent, or Firm — Young & Thompson

(57) ABSTRACT

An injectable hydrogel includes a hydrogel matrix based on (a) single-phase-type cross-linked biopolymer(s), characterized in that previously cross-linked biopolymer hydrogel particles are co-cross-linked with the matrix. A method of and a process for production of the above-mentioned hydrogel are also disclosed.

18 Claims, 1 Drawing Sheet

Figure 1:
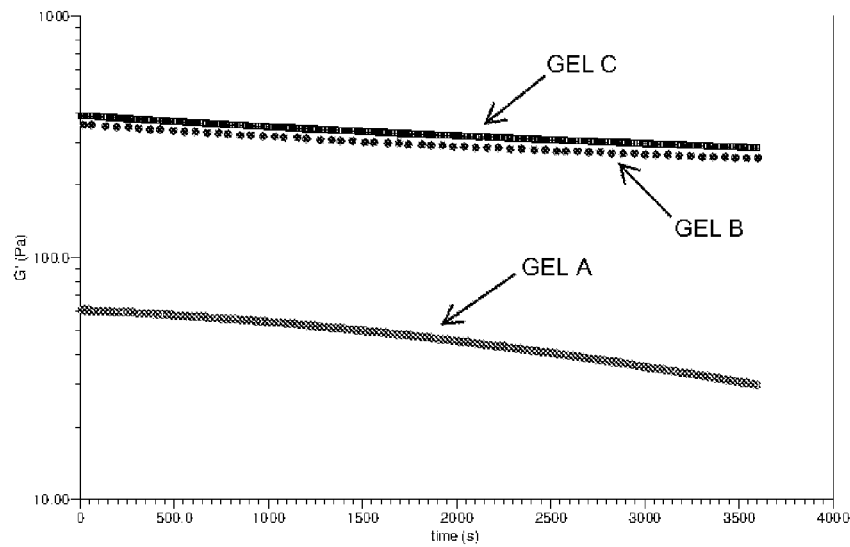

INJECTABLE HYDROGEL WITH AN ENHANCED REMANENCE AND WITH AN ENHANCED ABILITY TO CREATE VOLUME

BACKGROUND OF THE INVENTION

1. Field of the Invention

This invention relates to an injectable hydrogel that comprises a matrix based on (a) cross-linked biopolymer(s) (single-phase-type matrix) in which previously cross-linked biopolymer particles have been co-cross-linked.

This invention also relates to the process for production of injectable hydrogel.

This invention also has as its object the use of the above-mentioned hydrogel in therapeutic applications and in the dermato-cosmetic field.

2. Description of the Related Art

The use of viscoelastic products that are based on (a) cross-linked biopolymer(s) is common for separating, replacing or filling in a biological tissue or increasing the volume of said tissue or else supplementing or replacing a biological fluid.

Thus, the viscoelastic products that are based on (a) cross-linked biopolymer(s) are used in numerous therapeutic applications and in the dermato-cosmetic field.

For example, the viscoelastic products that are based on (a) cross-linked biopolymer(s) are used:

- in rheumatology, as a replacement agent, a temporary supplement of the synovial fluid,
- in urology/gynecology, as an agent that makes it possible to increase the volume of the sphincter or the urethra,
- in ophthalmology, as an adjuvant in cataract surgery or for glaucoma treatment,
- in pharmaceuticals, as a gel for releasing active substances,
- in surgery, for bone reconstruction, the increase of the volume of the vocal chords, or the production of surgical tissues,
- in dermato-cosmetics, for filling in wrinkles, masking scars or increasing the volume of the lips.

From the prior art, two large families of gels that are based on biodegradable biopolymers are known: the gels called "single-phase" and the gels called "two-phase."

Biopolymers are polymers that are present in living organisms or organisms that are synthesized by the latter; they are called biodegradable when they can be resorbed over time in the treated zone (zone into which they have been inserted or injected).

The single-phase gels, based on one or more cross-linked biodegradable biopolymers, such as sodium hyaluronate, come in the form of a single phase. These single-phase gels that are based on (a) biodegradable biopolymer(s) degrade over time, in a superficial way. This surface degradation occurs slowly, taking into account the cross-linked nature of these gels.

The two-phase gels comprise particles that consist of one or more cross-linked biopolymers (such as sodium hyaluronate), dispersed in a fluid phase, such as a physiological solution, a buffer solution, or a biopolymer-based solution. In this case, this fluid phase plays a vector role. For these two-phase gels, the degradation of the fluid phase is very quick. Injected intradermally, the half-life of this fluid phase is approximately 48 hours if it consists of non-cross-linked sodium hyaluronate. The degradation of the cross-linked particles is slow and occurs by surface degradation.

However, so as to ensure their function with effectiveness, the cross-linked biopolymer-based viscoelastic products and therefore the hydrogel of this invention should meet in particular the following requirements: to be injectable through a needle, to have a strong remanence (dwell time of the gel at the injection site), and to have a strong capacity to create volume when they are inserted into a tissue whose volume it is desired to increase.

The document FR2733426 describes a matrix that is designed to fill in wrinkles and that comprises: a biocompatible polymer, copolymerized by intercatenary bridging (cross-linking) and then transformed into microspheres, and a gel of the same polymer that may or may not be cross-linked. The microspheres can be suspended in the cross-linked gel.

The document WO00/01428 describes a process for preparation of two-phase compositions that first comprises the preparation of a continuous phase, such as a hydrogel with cross-linked hyaluronic acid. Then, the preparation of a dispersed phase in the form of particles obtained from a polymer hydrogel obtained by polymerization and cross-linking of acrylic acid and/or methacrylic acid and/or one of their derivatives is produced. Finally, these two phases—continuous phase and dispersed phase—are mixed.

SUMMARY OF THE INVENTION

This invention describes a new type of injectable gels, comprising a cross-linked biopolymer-based matrix (single-phase-type matrix) in which previously cross-linked biopolymer particles have been co-cross-linked.

This new type of hydrogel is different from single-phase and two-phase gels that are described above but also different from the gels that are described in the two documents that are cited above, gels in which particles or microspheres are simply dispersed and not co-cross-linked in a single-phase-type hydrogel matrix.

The hydrogel according to the invention can be injected through a needle, and it has an enhanced remanence and an enhanced ability to create volume relative to single-phase and two-phase biopolymer-based gels (see examples).

The remanence of an injectable hydrogel is a key characteristic of the product. It is important that this remanence be suited to the indication and, in most cases, a strong remanence is desired.

A hydrogel is degraded in vivo over time by different degradation factors. The primary degradation factors are as follows (more or less significant factors based on the indication): radical-type degradation, enzymatic degradation, thermal degradation, or mechanical degradation.

The remanence of the hydrogel according to the invention is primarily improved for the following two reasons:

It seems that the hydrogel according to the invention has a better resistance to the degradation than the single-phase or two-phase gels that are described above. The hydrogel according to the invention would in fact undergo slow surface degradation over time, which would involve a delayed appearance (and then optionally a slow release) of cross-linked particles that are imprisoned (sterically or by covalent bonds) in the 3D network of the single-phase-type cross-linked matrix. These particles would then be degraded over time by surface erosion.

During and after injection, the particles that are contained in a two-phase gel (cross-linked particles dispersed in a fluid phase) have a strong tendency to migrate. This migration induces a reduction of the effectiveness of the treatment at the treated zone. For a single-phase, cross-linked gel with simple dispersion of particles, these particles are sterically kept in the 3D matrix. For a gel according to the invention, the diffusion of the particles is significantly reduced relative to the above-mentioned gels because the particles are kept within the gel by steric occupancy but also by covalent bonds.

The ability to create the volume of the hydrogel according to the invention is enhanced relative to the single-phase and two-phase gels.

Actually, the hydrogel according to the invention is more dense, and its structure is reinforced relative to a single-phase gel: the presence of cross-linked particles within the single-phase-type matrix makes it possible, on the one hand, "to remove" the 3D network from the single-phase-type matrix, and, on the other hand, to significantly increase the overall elasticity of its structure.

Injected into a biological tissue, the hydrogel undergoes a mechanical stress. The hydrogel according to the invention, owing to its reinforced structure and its strong elasticity, has a better capacity for creation and holding the volume relative to a single-phase-type hydrogel.

In particular, the biopolymer(s) is (are) selected from the group that consists of: sodium hyaluronate, chondroitin sulfate, keratan, keratan sulfate, heparin, heparan sulfate, cellulose and its derivatives, alginates, xanthan, carrageenan, proteins or nucleic acids or mixtures thereof.

These biopolymers all have alcohol and/or carboxyl and/or amide and/or sulfate reactive functions, for example. Placed under good reaction conditions (in terms of pH, temperature, etc.), these reactive functions will be able to react with the added cross-linking agent(s), thus leading to the formation of covalent bonds (for instance, ethers, esters, or based on sulfur), and therefore to the cross-linking of biopolymers.

Even more preferably, one of the biopolymers that is used in this invention (for the preparation of particles and/or the preparation of the single-phase-type matrix) is sodium hyaluronate.

The total concentration of biopolymer of this invention is between 0.01 and 100 mg/ml and preferably between 10 and 40 mg/ml.

The hydrogel particles that are used in this invention have varied shapes: spherical, elliptical, or irregular shapes, or they have several of these shapes. Advantageously, these particles have an inside diameter of between 1 and 2,000 micrometers and preferably between 50 and 1,000 micrometers.

The percent by mass of particles in the single-phase-type matrix is between 1 and 99%.

The average size of the particles and the percent by mass of particles in the hydrogel according to the invention depend on the desired mechanical characteristics and the remanence sought for the targeted indication.

The hydrogel particles are advantageously distributed and co-cross-linked homogeneously inside the single-phase-type hydrogel matrix.

The hydrogel according to the invention can contain various common additives. By way of example, the pH modifiers and the osmolarity adjusters will be cited.

The hydrogel according to the invention can also contain any pharmacologically active agent. It can then constitute a gel for the controlled release of active ingredient. For example, a gel according to the invention that contains a steroidal anti-inflammatory agent such as triamcinolone acetonide will be cited.

The hydrogel according to the invention can also contain any active substance such as an anti-oxidizing agent or any substance that makes the gel better able to resist in vivo degradation. For example, the molecules of the polyol family will be cited.

Another object of this invention is a process for production of an injectable hydrogel, according to the characteristics above, characterized in that it comprises the stages that consist in:

Preparing cross-linked hydrogel particles,

Adding these cross-linked hydrogel particles during the primary cross-linking or the secondary cross-linking of the single-phase-type hydrogel matrix.

The cross-linked hydrogel particles are prepared according to the techniques that are well-known by one skilled in the art (see document US2005/0136122). For example, the particles can be obtained by mechanical grinding of a cross-linked single-phase gel.

To obtain a hydrogel according to the invention, the cross-linked hydrogel particles are added to the reaction medium during the production of a single-phase-type cross-linked matrix.

The single-phase-type cross-linked matrix is prepared according to the techniques that are described in the prior art (for example: WO 2005/085329, WO 2005/012364, WO 2004/092222).

The addition of the particles to the reaction medium is carried out according to two variants.

According to a first variant, the cross-linked hydrogel particles are added to the reaction medium during the primary cross-linking of the single-phase-type cross-linked matrix, i.e., before or after the first addition of cross-linking agent to the reaction mixture.

According to a second variant, the cross-linked hydrogel particles are added to the reaction medium under conditions of secondary cross-linking, by triggering a new cross-linking either on the basis of the remaining cross-linking agent still present from the primary cross-linking or by again adding a cross-linking agent to the reaction medium.

The cross-linking of the single-phase-type cross-linked matrix and the co-cross-linking of the particles are completely stopped during the elimination of the remaining cross-linking agent by purification of the gel.

The cross-linking agent(s) used for the cross-linking of the single-phase-type matrix and for the co-cross-linking of the particles are those that are described in the prior art. For example, a di-epoxy such as butanediol diglycidyl ether (BDDE) is used.

The cross-linking of the single-phase-type matrix and the co-cross-linking of the particles are carried out in a medium that can range from an acidic pH to a basic pH based on the type of cross-linking bonds desired.

The cross-linking of the single-phase-type matrix and the co-cross-linking of the particles are completely stopped during the elimination of the remaining cross-linking agent by purification, whereby the techniques for purification of a cross-linking gel are those that are well known by one skilled in the art: various deionized water baths, dialysis, . . . .

The cross-linking techniques are well known to one skilled in the art and will not be explained in further detail in this document.

The object of this document is also the use of an injectable hydrogel, according to the invention above, for separating, replacing or filling in a biological tissue or increasing the volume of said tissue or else supplementing or replacing a biological fluid.

Thus, the hydrogel of this invention is used in numerous therapeutic applications and in the dermato-cosmetic field.

For example, the hydrogel of this invention is used:
   in rheumatology, as a replacement agent, a temporary supplement of the synovial fluid, in urology/gynecology, as an agent that makes it possible to increase the volume of the sphincter or the urethra, in ophthalmology, as an adjuvant in cataract surgery or for glaucoma treatment, in pharmaceuticals, as a gel for releasing active substances, in surgery, for bone reconstruction, the increase of the volume of the vocal chords or the production of surgical tissues, in dermato-cosmetics, for filling in wrinkles, masking scars or increasing the volume of the lips.

BRIEF DESCRIPTION OF THE DRAWING FIGURES

The invention will be better understood and other objects, details, characteristics and advantages of the latter will appear more clearly during the following detailed explanatory description of several embodiments of the invention, provided purely by way of illustration and in a non-limiting manner, referring to the accompanying graphics.

Figure 2:
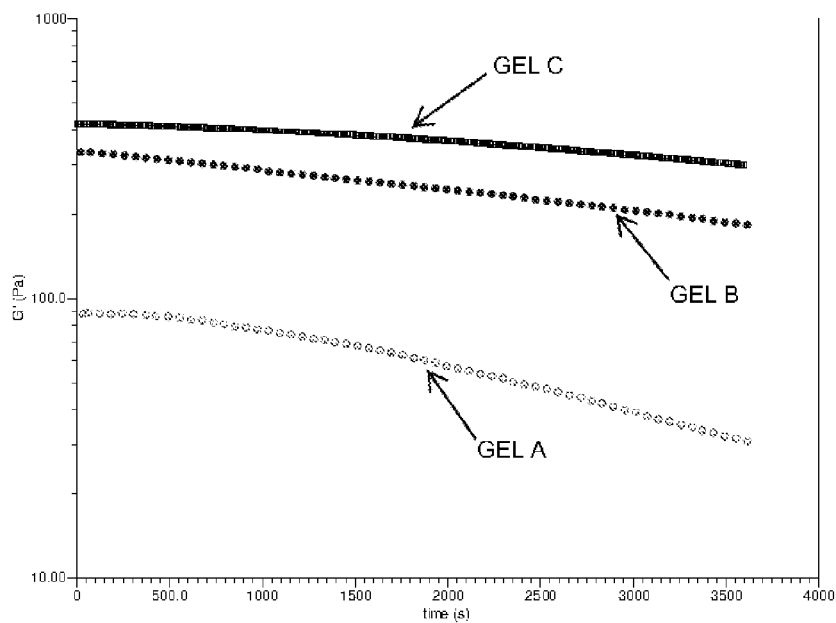

In these graphics:

FIG. 1 shows the value of the elastic module G' (Pa) of several gels A, B and C over time after the addition of an oxidizing agent to said gels, FIG. 2 shows the value of the elastic module G' (Pa) of the above-mentioned gels A, B and C over time but after the addition of a hyaluronidase solution to the gels to be tested.

DETAILED DESCRIPTION OF THE INVENTION

Examples are proposed for purposes of illustrating, but would in no case be interpreted as limiting, the scope of the invention.

Example 1

Production of a Single-Phase-Type Gel "A" (Prior Art)

3.5 g of sodium hyaluronate (MM=2.10$^6$ Da) is added to 30.5 ml of a 1% NaOH solution. The whole mixture is allowed to stand for 1 hour and then mixed with the spatula for 10 minutes. The cross-linking reaction is then triggered by adding 263 μl of butanediol diglycidyl ether (BDDE) to the solution, and the whole mixture is mixed with the spatula for 10 minutes. The reaction mixture is introduced into a water bath at 50° C. for 2 hours. The mixture is readjusted to the physiological pH using 1 M HCl. The volume is adjusted to 116 ml with a buffered solution at pH=7.

The thus obtained gel is then dialyzed for 24 hours (regenerated cellulose, separation limit: MM=60 kDa) against a buffered solution at pH=7.

The total concentration of sodium hyaluronate is 26 mg/ml.

The gel is filled into a 1 ml glass syringe and then sterilized in moist heat according to a cycle at 121° C. for 15 minutes.

Let "A" be the gel obtained.

Example 2

Preparation of Particles of Cross-Linked Hydrogel 3.5 g of sodium hyaluronate (MM=2.10$^6$ Da) is added to 24 ml of a 1% NaOH solution. The whole mixture is allowed to stand for 1 hour and then mixed with the spatula for 10 minutes. The cross-linking reaction is then triggered by adding 700 μl of butanediol diglycidyl ether (BDDE) to the solution, and the whole mixture is mixed with the spatula for 10 minutes. The reaction mixture is introduced into a water bath at 50° C. for 2 hours. The mixture is readjusted to the physiological pH using 1 M HCl. The volume is adjusted to 92 ml using a buffered solution at pH=7.

The single-phase gel is then transformed by mechanical grinding of particles with an equivalent mean diameter that is approximately equal to 200-300 μm.

Example 3

Production of a Gel "B" According to the Invention 3.5 g of sodium hyaluronate (MM=2.10$^6$ Da) is added to 5.5 ml of a 5.5% NaOH solution. 25 g of particles (prepared in Example 2) are also added to the solution.

The whole mixture is allowed to stand for 1 hour and then mixed with the spatula for 10 minutes. The cross-linking reaction is then triggered by adding 263 μl of butanediol diglycidyl ether (BDDE) to the solution, and the whole mixture is mixed with the spatula for 10 minutes. The reaction mixture is introduced into a water bath at 50° C. for 2 hours. The mixture is readjusted to the physiological pH using 1 M HCl. The volume is adjusted to 116 ml using a buffered solution at pH=7.

The thus obtained gel is then dialyzed for 24 hours (regenerated cellulose, separation limit: MM=60 kDa) against a buffered solution at pH=7.

The total concentration of sodium hyaluronate is 28 mg/ml.

The gel is filled into a 1 ml glass syringe and then sterilized in moist heat according to a cycle at 121° C. for 15 minutes.

Let "B" be the gel obtained.

Example 4

Production of a Gel "C" According to the Invention 3.5 g of sodium hyaluronate (MM=2.10$^6$ Da) is added to 30.5 ml of a 1% NaOH solution.

The whole mixture is allowed to stand for 1 hour and then mixed with the spatula for 10 minutes. The cross-linking reaction is then triggered by adding 263 μl of butanediol diglycidyl ether (BDDE) to the solution, and the whole mixture is mixed with the spatula for 10 minutes. The reaction mixture is introduced into a water bath at 50° C. for 2 hours.

58 g of particles (prepared in Example 2) and 24 ml of a 1% NaOH solution are added and then mixed with the spatula for 10 minutes.

The reaction still continues for 6 hours at 25° C. The pH is then adjusted to the physiological pH using 1 M HCl.

The thus obtained gel is then dialyzed for 24 hours (regenerated cellulose, separation limit: MM=60 kDa) against a buffered solution at pH=7.

The total concentration of sodium hyaluronate is 31 mg/ml.

The gel is filled into a 1 ml glass syringe and then sterilized in moist heat according to a cycle at 121° C. for 15 minutes.

Let "C" be the gel obtained.

Table for Comparison (Examples 1, 3 and 4)

a) pH/Osmolarity

| Gel | pH (25° C.) | Osmolarity (mOsm/kg) |
|---|---|---|
| A | 7.1 | 292 |
| B (According to the Invention) | 7.0 | 301 |
| C (According to the Invention) | 7.0 | 314 |

The gels A, B and C are isotonic and have a neutral pH.

b) Ejection Force

The ejection force corresponds to the measurement of the force that is necessary for extruding the gel from the syringe at a rate of 12.5 mm/minute through a needle of 27 G½.

| Gel | Ejection Force (N) |
| --- | --- |
| A | 41 |
| B (According to the Invention) | 61 |
| C (According to the Invention) | 42 |

The gels A, B and C can be injected.

c) Rheological Properties

The rheological properties of the gel are studied using an AR 1000 rheometer (TA Instruments) with a flat geometry of 40 mm, an air gap of 1,000 microns, and an analytical temperature of 25° C.

The values of the parameters G' that are measured at 1 Hz are compared for the 3 gels.

| Gel | G' (1 Hz) |
| --- | --- |
| A | 108 |
| B (According to the Invention) | 352 |
| C (According to the Invention) | 441 |

The gels B and C (according to the invention) have a very strong elasticity (very high G' (1 Hz)).

Thanks to their strong elasticity, the gels B and C have a better ability to create and maintain the volume relative to the single-phase-type gel A.

d) Remanence Tests (FIGS. 1 and 2)

The remanence of the gel is studied using an AR1000 rheometer (TA Instruments) with a flat geometry of 40 mm and an air gap of 1,000 microns.

The degradation test 1 is carried out by adding an oxidizing agent to the gel to be tested, by homogenizing the mixture with the spatula for 1 minute, by being brought to a temperature of 37° C., and by imposing a deformation of 0.3%. The value of the parameter G' at 1 Hz is measured over time. The thus obtained rheology curves are provided in FIG. 1.

It is noted that the gels according to the invention have a very strong remanence. Despite the radical/thermal/mechanical degradation, they preserve their high elasticity level (G') over a long period.

The degradation test 2 is carried out by adding a hyaluronidase solution to the gel that is to be tested, by homogenizing with the spatula for 1 minute, by being brought to a temperature of 37° C., and by imposing a deformation of 0.3%. The value of the parameter G' at 1 Hz is measured over time.

The thus obtained rheology curves are provided in FIG. 2. It is noted that the gels according to the invention have a very strong remanence. Despite the enzymatic/thermal/mechanical degradation, they preserve their high level of elasticity (G') over a long period.

The invention claimed is:

1. An injectable hydrogel that comprises:
a hydrogel matrix comprising single phase cross-linked biopolymer(s), and
previously cross-linked biopolymer hydrogel particles co-cross-linked with said matrix,
wherein the biopolymer(s) is (are) selected from the group consisting of sodium hyaluronate, chondroitin sulfate, keratan, keratan sulfate, heparin, heparan sulfate, cellulose and its derivatives, alginates, xanthan, carrageenan, proteins, nucleic acids and mixtures thereof,
the total biopolymer concentration is between 0.01 and 100 mg/ml,
the mass percent of particles in the single-phase matrix is between 1 and 99%, and
the particles have an inside diameter of between 50 and 1000 micrometers.

2. The injectable hydrogel according to claim 1, wherein the biopolymer is sodium hyaluronate.

3. The injectable hydrogel according to claim 1, wherein the hydrogel particles have the following shapes: spherical, elliptical, or irregular shapes, or they have several of these shapes.

4. The injectable hydrogel according to claim 1, wherein the biopolymer particles are distributed and co-cross-linked homogeneously inside the hydrogel matrix.

5. The injectable hydrogel according to claim 1, further comprising at least one additive.

6. The injectable hydrogel according to claim 1, further comprising at least one pharmacologically active agent.

7. The injectable hydrogel according to claim 1, wherein the total biopolymer concentration is between 10 and 40 mg/ml.

8. The injectable hydrogel according to claim 1, further comprising at least one additive.

9. The injectable hydrogel according to claim 6, wherein the at least one pharmacologically active agent is a steroidal anti-inflammatory agent.

10. The injectable hydrogel according to claim 1, further comprising at least one anti-oxidizing agent.

11. The injectable hydrogel according to claim 1, further comprising at least one compound that makes the gel better able to resist in vivo degradation.

12. The injectable hydrogel according to claim 11, wherein the at least one compound is a polyol.

13. The injectable hydrogel according to claim 1, having an osmolarity of 301-314 mOsm/kg.

14. The injectable hydrogel according to claim 1, having an ejection force of 42-61 N.

15. The injectable hydrogel according to claim 1, having an elasticity of 352-441 G' at 1 Hz.

16. The injectable hydrogel according to claim 8, wherein the at least one additive is a pH modifier or an osmolarity adjuster.

17. The injectable hydrogel according to claim 9, wherein the steroidal anti-inflammatory is triamcinolone acetonide.

18. The injectable hydrogel according to claim 1, wherein the cross-linking agent is butanediol diglycidyl ether.

* * * * *